United States Patent [19]

Hosomi

[11] Patent Number: 4,946,955

[45] Date of Patent: Aug. 7, 1990

[54] METHOD FOR THE PREPARATION OF POLYCYCLIC 1,3-THIAZOLIDINES

[75] Inventor: Akira Hosomi, Nagasaki, Japan

[73] Assignee: Toray Silicone Company Limited, Tokyo, Japan

[21] Appl. No.: 242,470

[22] Filed: Sep. 9, 1988

[30] Foreign Application Priority Data

Sep. 11, 1987 [JP] Japan .................. 62-227986

[51] Int. Cl.$^5$ .......................... C07D 513/08
[52] U.S. Cl. ...................... 544/234; 544/250; 544/343; 544/346; 544/235; 546/62; 546/84; 546/114; 546/14; 548/148; 548/149; 548/150; 548/151; 548/154
[58] Field of Search ............ 544/234, 250; 546/62, 546/84, 114, 14; 548/148, 149, 150, 151, 154

[56] References Cited

PUBLICATIONS

CA:107:198156z, "Intramolecular Cyclization . . . "

Abstract of J. Org. Chem. 1987, 52(19)4423-4 (1987) Hosami, Hayashi, Hoashi, Kohra and Tominaga.

*Primary Examiner*—Christine M. Nucker
*Assistant Examiner*—Frederick F. Tsung
*Attorney, Agent, or Firm*—Carl A. Yorimoto; Roger E. Gobrogge

[57] ABSTRACT

A method for preparation of polycyclic 1,3-thiazolidines is described. The method comprises reacting a fluoride ion source, in a solvent, with an onium salt synthesized by the reaction of a nitrogenous heteroaromatic compound with a halomethyl trimethylsilylmethyl sulfide, the halomethyl trimethylsilylmethyl sulfide being selected from the group consisting of chloromethyl trimethylsilylmethyl sulfide, bromomethyl trimethylsilylmethyl sulfide, or iodomethyl trimethylsilylmethyl sulfide.

15 Claims, No Drawings

METHOD FOR THE PREPARATION OF POLYCYCLIC 1,3-THIAZOLIDINES

BACKGROUND OF THE INVENTION

The instant invention relates to a method for the preparation of polycyclic 1,3-thiazolidines.

Several methods are known for the preparation of 1,3-thiazolidines such as, for example, the reaction at room temperature of cysteamine hydrochloride with aqueous formaldehyde solution, and the reaction of ethyleneimine with ketone or aldehyde under the action of sulfur or hydrogen sulfide. However, these prior methods of preparation are directed at the preparation of monocyclic 1,3-thiazolidines and cannot provide polycyclic 1,3-thiazolidines.

SUMMARY OF THE INVENTION

The instant invention is achieved by the inventors as the result of extensive research into methods for the preparation of polycyclic 1,3-thiazolidines.

The object of the present invention is to provide a simple method for the preparation of polycyclic 1,3-thiazolidines.

The object is achieved by the action, in acetonitrile or tetrahydrofuran, of fluoride ion on the onium salt synthesized by the reaction of a nitrogenous heteroaromatic compound with a halomethyl trimethylsilylmethyl sulfide. The instant invention, because it consists of the reaction of fluoride ion in acetonitrile or tetrahydrofuran with the onium salt synthesized by the reaction of halomethyl trimethylsilylmethyl sulfide (the halomethyl group being chloromethyl, bromomethyl or iodomethyl) with a nitrogenous heteroaromatic compound, has the remarkable effect of providing a high-yield synthesis of polycyclic 1,3-thiazolidines under mild conditions.

DESCRIPTION OF THE INVENTION

In accordance with the instant invention there is provided a method for preparation of polycyclic 1,3-thiazolidines under conditions that will be delineated herein. What is described, therefore, is a method for preparation of polycyclic 1,3-thiazolidines, the method comprising reacting a fluoride ion source, in a solvent, with an onium salt synthesized by the reaction of a nitrogenous heteroaromatic compound with a halomethyl trimethylsilylmethyl sulfide, the halomethyl trimethylsilylmethyl sulfide being selected from a group consisting of chloromethyl trimethylsilylmethyl sulfide, bromomethyl trimethylsilylmethyl sulfide, or iodomethyl trimethylsilylmethyl sulfide.

The halomethyl trimethylsilylmethyl sulfide which constitutes one of the starting materials in onium salt synthesis is a compound with the formula, (CH$_3$)$_3$SiCH$_2$SCH$_2$X, wherein X is a chlorine, bromine, or iodine atom. When considered from the viewpoint of reactivity, preferred halomethyl trimethylsilylmethyl sulfides are chloromethyl trimethylsilylmethyl sulfide and then bromomethyl trimethylsilylmethyl sulfide.

The halomethyl trimethylsilylmethyl sulfide is readily synthesized by passing dry hydrogen halide for several hours with ice cooling through a mixture of trimethylsilylmethylthiol and trioxane. This is followed by the addition of hexane, dehydration, removal of the hexane, and distillation.

The nitrogenous heteroaromatic compound comprising the other starting material in onium salt synthesis must have at least one tertiary nitrogen atom in an unsaturated ring and must have a double bond between said nitrogen atom and an adjacent carbon atom. Both monocyclic and polycyclic compounds are suitable. Examples of such nitrogenous heteroaromatic compounds are pyridine, 3,5-lutidine, quinoline, isoquinoline, phthalazine, and phenanthridine. It is preferred that the nitrogenous heteroaromatic compound be dried prior to its introduction into the reaction.

The onium salt is synthesized from the halomethyl trimethylsilylmethyl sulfide and nitrogenous heteroaromatic compound by mixing the two reactants, which are introduced into the reactor at a molar ratio between the former and latter in a range from 1.1:1.0 to 1.3:1.0. The onium salt, obtained by heating for 4 to 15 hours at 40° to 80° C. with stirring and exclusion of moisture, is collected by filtration and washed with a dry solvent which will not dissolve the onium salt but which will dissolve the starting materials. Examples of such solvents are dry acetone, hexane, and carbon tetrachloride. The reaction in this case can also be run after dissolving the two reactants in dry acetonitrile or tetrahydrofuran.

The mechanism by which the onium salt is obtained from the halomethyl trimethylsilylmethyl sulfide and nitrogenous heteroaromatic compound is explained below for the example of chloromethyl trimethylsilylmethyl sulfide and pyridine.

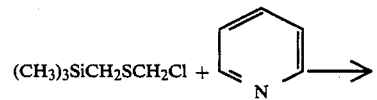

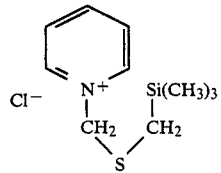

To synthesize the polycyclic 1,3-thiazolidine by the action of fluoride ion on this onium salt in acetonitrile or tetrahydrofuran, the onium salt, fluoride ion source, and acetonitrile or tetrahydrofuran are placed in a reactor and stirred with the exclusion of moisture.

Examples of fluoride ion sources are cesium fluoride, rubidium fluoride, lithium fluoride, (n-C$_4$H$_9$)$_4$NF, and KF-18-crown-6. The molar ratio between the fluoride ion source and onium salt is preferably in a range from about 1:1 to 3:1.

The fluoride ion source, acetonitrile, and tetrahydrofuran are preferably preliminarily dried.

The reaction temperature is preferably room temperature, but warming up to about 80° C. is permissible. The reaction time will vary with the reaction temperature and the type of starting nitrogenous heteroaromatic compound. It will typically exceed 10 hours for reactions at room temperature. While it will generally require 20 to 80 hours, as long as 200 hours or more may be required.

The polycyclic 1,3-thiazolidine is then isolated from the reaction solution after completion of the reaction.

Because polycyclic 1,3-thiazolidines are soluble in acetonitrile or tetrahydrofuran along with unreacted starting materials and by-products, ether plus water or preferably aqueous sodium bicarbonate is first added, this is shaken, and the ether layer is separated after standing. After this step has been repeated two to three times, the ether layer is dried over a dehydrating agent and the ether is then removed. The residue is then fractionated by thin-layer chromatography or gas chromatography.

The mechanism for the production of polycyclic 1,3-thiazolidines by the action of fluoride ion on the onium salt is theorized by the inventors to be as follows (explained using the onium salt of pyridine).

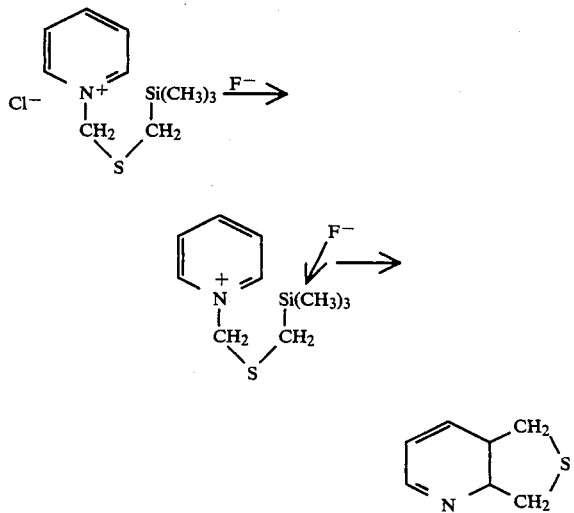

Furthermore, while the preceding explanation involves isolation of the onium salt prior to the reaction with fluoride ion, it is to be understood that it will also be possible to carry out the reaction with fluoride ion directly after onium salt synthesis without isolation of the onium salt. This theory is not to be construed as limiting the invention described herein.

So that those skilled in the art may better understand and appreciate the instant invention, the following examples are presented. These examples are presented to be illustrative and are not to be construed as limiting the claims of the invention presented herein.

The instant invention will be explained on the basis of reference and illustrative examples. In the reference and illustrative examples, the infrared absorption spectrum (IR) was taken using the KBr tablet method, the ultraviolet absorption spectrum (UV) was measured in 95% ethanol, the nuclear magnetic resonance spectrum ($^1$HNMR) was measured using tetramethylsilane as an internal reference, and the mass spectrum (MS) was taken using low-resolution and high-resolution mass analysis.

REFERENCE EXAMPLE

Synthesis of Chloromethyl Trimethylsilylmethyl Sulfide 12.0 g (0.10 mol) trimethylsilylmethylthiol and 3.2 g (0.035 mol) trioxane were added to and mixed in a round-bottom flask. Dry hydrogen chloride was passed through the mixture for 4 hours with ice cooling. 50 ml hexane was then added, and the hexane was removed after drying over sodium sulfate.

Distillation afforded 11.7 g (0.069 mol) of the target chloromethyl trimethylsilylmethyl sulfide. The distilled product had a boiling point of 75° C. at 20 mmHg. Analytical results are as follow:

$^1$HNMR (CCl$_4$): delta 0.01 (s, 9H), 2.00 (s, 2H), 4.80 (s, 2H).

Elemental analysis: C 35.81 (calculated value 35.59) H 7.93 (calculated value 7.76).

Mass spectral data (m/z) 70 eV: 170 (6), 168 (M+, 14), 153 (7), 133 (6), 120 (5), 11.9 (37), 95 (13), 93 (33), 79 (10), 75 (8), 74 (9), 73 (100), 61 (5), 60 (70), 59 (16), 46 (7), 45 (20), 44 (23), 43 (15).

EXAMPLES 1 THROUGH 6

Six runs were made in which 2.03 g (12 mmol) chloromethyl trimethylsilylmethyl sulfide and 10 mmol of a nitrogenous heteroaromatic compound were placed in a round-bottom flask, and the atmosphere in the flask was replaced with dry nitrogen. Upon heating the flask for one hour at 60° C. with stirring, the onium salt separated as crystals. The crystals were collected by filtration and washed with dry acetone.

The washed crystals were again placed in a round-bottom flask, followed by the addition of 1.52 g (10 mmol) dry cesium fluoride and 50 cc dry acetonitrile. The atmosphere in the flask was replaced with dry nitrogen, and the flask was then stirred, for times varying with each run, at room temperature.

After the completion of stirring, 50 cc water and 300 cc diethyl ether were added, this was shaken, and the diethyl ether layer was separated after standing. This step was repeated a total of three times. The ether layer was dried over sodium sulfate and the ether was then removed.

Silica gel thin-layer chromatography yielded the pure polycyclic 1,3-thiazolidine.

The respective starting nitrogenous heteroaromatic compounds, the yields of the onium salts, the stirring times, the chemical structural formulas of the polycyclic 1,3-thiazolidine products, and their yields are reported in Table 1. In Table 1, the onium salts formed for each run are identified as number (3a), (3b), (3c), (3d), (3e), and (3f), respectively, corresponding to Examples 1, 2, 3, 4, 5, and 6, respectively. Further in Table 1, the polycyclic 1,3-thiazolidine products generated in each run are identified as number (4a), (4b), (4c), (4d), (4e), and (4f), respectively, corresponding to Examples 1, 2, 3, 4, 5, and 6, respectively.

The chemical name of each onium salt and polycyclic 1,3-thiazolidine, their properties, and the corresponding analytical data are reported below. Onium Salts:

(3a) 1-(trimethylsilylmethylthiomethyl)pyridinium chloride

Melting point: 115° C., colorless crystals (needles).

IR (KBr, cm$^{-1}$): 3040, 2960, 1630, 1490, 1242, 1158, 850, 720, 680.

UV (EtOH, lambda max, nm (log epsilon)): 220 (3.76), 261 (3.60).

$^1$HNMR (90 MHz, DMSO-d$_6$): delta 0.03 (9H, s, SiMe$_3$), 1.94 (2H, s, S-CH$_2$-Si), 5.92 (2H, s, N-CH$_2$-S), 8.13–8.28 (2H, m, 3, 5-H), 8.56–8.82 (1H, m, 4-H), 9.30 (2H, dd, J=1.5, 7.0 Hz, 2, 6-H).

Elemental analysis of C$_{10}$H$_{18}$ClNSSi. Calculated: C 48.46, H 7.32, N 5.65. Found: C 48.16, H 7.18, N 5.58.

(3b) 2,3-dimethyl-1-(trimethylsilylmethylthiomethyl)-pyridinium chloride

Melting Point: 88° C., colorless crystals (needles).

IR (KBr, cm$^{-1}$): 3040, 3000, 2930, 1620, 1495, 850.

UV (EtOH, lambda max, nm (log epsilon)): 228 (3.67), 275 (3.61).

$^1$HNMR (90 MHz, DMSO-d$_6$): delta 0.00 (9H, s, SiMe$_3$), 1.93 (2H, s, S-CH$_2$-Si), 5.72 (2H, s, N-CH$_2$-S), 8.33 (1H, s, 4-H), 8.96 (2H, s, 2, 6-H).

Elemental analysis of C$_{12}$H$_{22}$ClNSSi.5/6H$_2$O: Calculated: C 49.54, H 8.20, N 4.81. Found: C 49.58, H 7.95, N 5.03.

(3c) 1-(trimethylsilylmethylthiomethyl)quinolinium chloride

Melting Point: 135° C., colorless crystals (needles).

IR (KBr, cm$^{-1}$): 2950, 1590, 1552, 3060, 1242, 850.

UV (EtOH, lambda max, nm (log epsilon)): 238 (4.45), 315 (3.83).

$^1$HNMR (90 MHz, DMSO-d$_6$): delta 0.01 (9H, s, SiMe$_3$), 1.96 (2H, s, S-CH$_2$-Si), 6.34 (2H, s, N-CH$_2$-S), 7.97–8.70 (5H, m, 3, 5, 6, 7, 8-H), 9.37 (1H, d, J=8.4 Hz, 4-H), 9.73 (1H, dd, J=1.3, 5.9 Hz, 2-H).

Elemental Analysis of C$_{14}$H$_{20}$ClNSSi: Calculated: C 56.44, H 6.77, N 4.70. Found: C 56.44, H 6.84, N 4.37.

(3d) 2-(trimethylsilylmethylthiomethyl)isoquinolinium chloride

Melting Point: 135° C., colorless crystals (needles).

IR (KBr, cm$^{-1}$): 3040, 2990, 1640, 1395, 1250, 843.

UV (EtOH, lambda max, nm (log epsilon)): 217 (4.54), 238 (4.60), 272 (3.52), 280 (sh, 3.51), 321 (3.57), 340 (sh, 3.51).

$^1$HNMR (90 MHz, DMSO-d$_6$): delta 0.00 (9H, s, SiMe$_3$), 1.99 (2H, s, S-CH$_2$-Si), 5.97 (2H, s, N-CH$_2$-S), 7.98–8.60 (4H, m, 5, 6, 7, 8-H), 8.64 (1H, d, J=6.8 Hz, 3-H), 8.91 (1H, dd, J=1.5, 6.8 Hz, 4-H), 10.29 (1H, s, 1-H).

Elemental Analysis of C$_{14}$H$_{20}$ClNSSi: Calculated: C 56.44, H 6.77, N 4.70. Found: C 56.56, H 6.57, N 5.01.

(3e) 2-(trimethylsilylmethylthiomethyl)phthalazinium chloride

Melting Point: 160° C., colorless crystals (needles).

IR (KBr, cm$^{-1}$): 2970, 1480, 1392, 850.

UV (EtOH, lambda max, nm (log epsilon)): 238 (4.01), 310 (3.97).

$^1$HNMR (90 MHz, DMSO-d$_6$): delta 0.05 (8H, s, SiMe$_3$), 2.14 (2H, s, S-CH$_2$-Si), 6.00 (2H, s, N-CH$_2$-S), 8.39–8.76 (4H, m, 5, 6, 7, 8-H), 10.15 (1H, s, 4-H), 10.90 (1H, s, 1-H).

Elemental Analysis of C$_{13}$H$_{19}$ClN$_2$SSi: Calculated: C 52.24, H 6.41, N 9.37. Found: C 52.78, H 6.22, N 9.45.

(3f) 5-(trimethylsilylmethylthiomethyl)phenanthridinium chloride

Melting Point: 205° C., colorless crystals (needles).

IR (KBr, cm$^{-1}$): 2950, 1619, 1245, 650.

UV (EtOH, lambda max, nm (log epsilon)): 248 (4.51), 273 (shoulder, 4.08), 332 (3.87).

$^1$HNMR (90 MHz, DMSO-d$_6$): delta 0.01 (9H, s, SiMe$_3$), 2.06 (2H, s, S-CH$_2$-Si), 6.31 (2H, s, N-CH$_2$-S), 7.81–9.20 (8H, m, 1, 2, 3, 4, 7, 8, 9, 10-H), 10.50 (1H, s, 6-H).

Elemental Analysis of C$_{18}$H$_{22}$ClNSSi: Calculated: C 62.13, H 6.37, N 4.03. Found: C 62.27, H 6.26, N 4.11.

Polycyclic 1,3-Thiazolidines:

(4a) 1,8a-dihydro-3H-thiazolo[3,4-a]pyridine

Yellowish-brown caramel.

$^1$HNMR (90 MHz, CDCl$_3$): delta 2.83 (1H, d, J=9.2 Hz, 1-H), 2.88 (1H, d, J=6.2 Hz, 1-H), 3.48–3.72 (1H, m, 8a-H), 4.17 (1H, d, J=9.2 Hz, 3-H), 4.51 (1H, d, J=9.2 Hz, 3-H), 4.85–5.01 (1H, m, 8-H), 5.58–6.07 (3H, m, 5, 6, 7-H).

MS: m/z 139 (15, M$^+$), 94 (8), 93 (100), 92 (11), 78 (5), 67 (5), 66 (17), 65 (12), 52 (5), 51 (6).

High-resolution mass spectral data: Calculated for C$_7$H$_9$NS: 139.0455. Found: 139.0484.

(4b) 1,8a-dihydro-6,8-dimethyl-3H-thiazolo[3,4-a]pyridine

Yellowish-brown caramel.

$^1$HNMR (90 MHz, CDCl$_3$): delta 1.64 (3H, d, J=1.3 Hz, 6-Me), 1.89 (3H, ws, 8-Me), 2.60 (1H, dd, J=9.0, 9.0 Hz, 1-H), 3.00 (1H, dd, J=6.4, 9.0 Hz, 1-H), 3.34 (1H, dd, J=6.4, 9.0 Hz, 8a-H), 4.15 (1H, d, J=9.0 Hz, 3-H), 4.44 (1H, d, J=9.0 Hz, 3-H), 5.41 (1H, bs, 7-H), 5.59 (1H, bs, 5-H).

MS: m/z 167 (18, M$^+$), 122 (10), 121 (100), 107 (6), 106 (14), 79 (11), 77 (9), 64 (7).

High-resolution mass spectral data: Calculated for C$_9$H$_{13}$NS: 167.0768. Found: 167.0792.

(4c) 3,3a-dihydro-1H-thiazolo[3,4-a]quinoline

Yellowish-brown caramel.

$^1$HNMR (90 MHz, CDCl$_3$): delta 2.67–3.17 (2H, m, 3-CH$_2$-), 3.95 (1H, d, J=8.2 Hz, 1-H), 3.95–4.23 (1H, m, 3a-H), 4.75 (1H, d, J=8.2 Hz, 1-H), 5.67 (1H, dd, J=8.2, 10.0 Hz, 4-H), 6.17–7.00 (5H, m, 5, 6, 7, 8, 9-H).

MS: m/z 189 (M$^+$, 23), 144 (13), 143 (100), 129 (30), 115 (10).

High-resolution mass spectral data: Calculated for C$_{11}$H$_{11}$NS: 189.0621. Found: 189.0608.

(4d) 1,10b-dihydro-3H-thiazolo[4,3-a]isoquinoline

Melting Point: 72° C. Yellowish-brown crystals (prisms).

IR (KBr, cm$^{-1}$): 1620, 1142, 763, 660.

UV (EtOH, lambda max, nm (log epsilon)): 239 (4.09), 310 (3.94).

$^1$HNMR (90 MHz, CDCl$_3$): delta 2.97 (1H, d, J=9.2 Hz, 1-H), 2.98 (1H, d, J=6.8 Hz, 1-H), 4.18 (1H, dd, J=6.8, 9.2 Hz, 10b-H), 4.38 (1H, d, J=9.2 Hz, 3-H), 4.58 (1H, d, J=9.2 Hz, 3-H), 5.55 (1H, d, J=7.7 Hz, 5-H), 5.97 (1H, dd, J=0.9, 7.7 Hz, 6-H), 6.97–7.32 (4H, m, 7, 8, 9-H).

MS: m/z 189 (M$^+$, 18), 143 (100), 131 (26), 115 (31), 69 (84).

High-resolution mass spectral data: Calculated for C$_{11}$H$_{11}$NS: 189.0612. Found: 189.0619.

Elemental Analysis for C$_{11}$H$_{11}$NS: Calculated: C 69.80, H 5.86, N 7.40. Found: C 69.47, H 5.57, N 7.30.

(4e) 1,10b-dihydro-3H-thiazolo[4,3-a]phthalazine

Yellowish-brown caramel.

$^1$HNMR (90 MHz, CDCl$_3$): delta 2.72–3.18 (2H, m, 1-CH$_2$), 4.13–4.25 (1H, m, 10b-H), 4.61 (1H, d, J=9.7 Hz, 3-H), 5.08 (1H, d, J=9.7 Hz, 3-H), 7.29–7.46 (5H, m, 5, 6, 7, 8, 9, 10-H).

MS: m/z 190 (M$^+$, 36), 173 (27), 145 (27), 144 (100), 143 (25), 133 (18), 130 (73), 117 (26), 116 (18), 103 (15), 76 (21), 73 (23).

High-resolution mass spectral data: Calculated for C$_{10}$H$_{10}$N$_2$S: 190.0565. Found: 190.0552.

(4f) 1,12b-dihydro-3H-thiazolo[4,3-f]phenanthridine

Yellowish-brown caramel.

TABLE 1

| Example No. | nitrogenous heteroaromatic Compound | onion salt No. | yield | stirring time(hr) | polycyclic 1,3-thiazolidine no. | Chemical structural Formula | yield |
|---|---|---|---|---|---|---|---|
| 1 | pyridine | (3a) | 94 | 25 | (4a) | [structure] | 96 |
| 2 | 3,5-dimethylpyridine | (3b) | 91 | 70 | (4b) | [structure] | 91 |
| 3 | quinoline | (3c) | 98 | 45 | (4c) | [structure] | 95 |
| 4 | isoquinoline | (3d) | 98 | 48 | (4d) | [structure] | 91 |
| 5 | phthalazine | (3e) | 96 | 48 | (4e) | [structure] | 92 |
| 6 | phenanthridine | (3f) | 75 | 234 | (4f) | [structure] | 43 |

$^1$HNMR (90 MHz, CDCl$_3$): delta 3.36 (1H, d, J=9.7 Hz, 1-H), 3.24–3.41 (2H, m, 3-CH$_2$), 4.27 (1H, d, J=9.7 Hz, 3-H), 4.35–4.54 (1H, m, 12b-H), 5.23 (1H, d, J=9.7 Hz, 3-H), 6.83–7.40 (5H, m, 6, 7, 10, 11, 12-H), 7.80–7.95 (3H, m, 5, 8, 9-H).

MS: m/z 239 (M+, 17), 194 (13), 193 (71), 84 (76), 66 (100).

High-resolution mass spectral data: Calculated for C$_{15}$H$_{13}$NS: 239.0769. Found: 239.0761.

EXAMPLE 7

169 mg (1.0 mmol) chloromethyl trimethylsilylmethyl sulfide and 79 mg (1 mmol) dry pyridine were placed in a 50 ml round-bottom flask, the atmosphere in the flask was replaced with dry nitrogen, and the flask was stirred for 1 hour at 60° to 70° C.; the onium salt separated as crystals.

304 mg (2 mmol) dry cesium fluoride and 10 ml dry acetonitrile were rapidly added to the reaction mixture, and stirring was continued at room temperature for 24 hours.

20 ml dimethyl ether and 10 ml saturated aqueous sodium bicarbonate were added, followed by stirring for 1 hour. The ether layer was separated after standing, and the aqueous layer was also extracted with dimethyl ether (three extractions with 10 ml per extraction).

The ether layers were combined and dried over anhydrous sodium sulfate, and the ether was then removed on a rotary evaporator. The residue was subjected to thin-layer chromatography to afford 134 mg (0.96 mmol, 96% yield) 1,8a-dihydro-3H-thiazolo[3,4-a]pyridine.

What is claimed is:

1. A method for preparation of polycyclic 1,3-thiazolidines, the method comprising reacting a fluoride ion source, in a solvent, with an onium salt synthesized by the reaction of a nitrogenous heteroaromatic compound having at least one tertiary nitrogen atom in an unsaturated ring, said nitrogen atom being attached to an adjacent carbon atom by a double bond, with halomethyl trimethylsilylmethyl sulfide, the halomethyl trimethylsilylmethyl sulfide being selected from a group consisting of chloromethyl trimethylsilylmethyl sulfide, bromomethyl trimethylsilylmethyl sulfide, or iodomethyl trimethylsilylmethyl sulfide.

2. A method for preparation of polycyclic 1,3-thiazolidines as described in claim 1, wherein the halomethyl trimethylsilylmethyl sulfide is selected from a group consisting of chloromethyl trimethylsilylmethyl sulfide or bromomethyl trimethylsilylmethyl sulfide.

3. A method for preparation of polycyclic 1,3-thiazolidines as described in claim 1, wherein the halomethyl trimethylsilylmethyl sulfide is chloromethyl trimethylsilylmethyl sulfide.

4. A method for preparation of polycyclic 1,3-thiazolidines as described in claim 1, wherein the fluoride ion source is cesium fluoride.

5. A method for preparation of polycyclic 1,3-thiazolidines as described in claim 1, wherein the solvent is selected from a group consisting of acetonitrile or tetrahydrofuran.

6. A method for preparation of polycyclic 1,3-thiazolidines as described in claim 1, wherein the molar ratio of the halomethyl trimethylsilylmethyl sulfide relative to the nitrogenous heteroaromatic compound is in a range from about 1.1:1 to 1.3:1.

7. A method for preparation of polycyclic 1,3-thiazolidines as described in claim 1, wherein the molar ratio of the fluoride ion source relative to the onium salt is in a range from about 1.0:1 to 3.0:1.

8. A method for preparation of polycyclic 1,3-thiazolidines as described in claim 1, wherein the onium salt is synthesized in a heated reaction and said onium salt is subjected to the action of the fluoride ion at room temperature or greater.

9. A method for preparation of polycyclic 1,3-thiazolidines as described in claim 8, wherein the onium salt is synthesized at a temperature in a range from about 40° to 80° C.

10. A method for preparation of polycyclic 1,3-thiazolidines as described in claim 8, wherein the onium salt is subjected to the action of the fluoride ion at a temperature less than about 80° C.

11. A method for preparation of polycyclic 1,3-thiazolidines as described in claim 1, wherein the onium salt is synthesized over a time greater than about 1 hour.

12. A method for preparation of polycyclic 1,3-thiazolidines as described in claim 11, wherein the onium salt is synthesized in a time in a range of from about 4 to 15 hours.

13. A method for preparation of polycyclic 1,3-thiazolidines as described in claim 1, wherein the onium salt is subjected to the action of the fluoride ion for a time of greater than about 10 hours.

14. A method for preparation of polycyclic 1,3-thiazolidines as described in claim 13, wherein the onium salt is subjected to the action of the fluoride ion for a time in a range from about 20 to 200 hours.

15. The method of claim 1 wherein the nitrogenous heteroaromatic compound is selected from the group consisting of pyridine, 3,5-lutidine, quinoline, isoquinoline, phthalazine, and phenanthridine.

* * * * *